(12) United States Patent
Nolan et al.

(10) Patent No.: US 6,800,484 B2
(45) Date of Patent: Oct. 5, 2004

(54) HIGH EFFICIENCY TRANSFECTION BASED ON LOW ELECTRIC FIELD STRENGTH, LONG PULSE LENGTH

(75) Inventors: Ed Nolan, San Diego, CA (US); Robin Filshie, Toronto (CA)

(73) Assignee: Genetronics, Inc., San Diego, CA (US)

(*) Notice: Subject to any disclaimer, the term of this patent is extended or adjusted under 35 U.S.C. 154(b) by 64 days.

(21) Appl. No.: 10/115,230

(22) Filed: Apr. 2, 2002

(65) Prior Publication Data

US 2002/0146831 A1 Oct. 10, 2002

(Under 37 CFR 1.47)

Related U.S. Application Data

(60) Division of application No. 09/342,024, filed as application No. PCT/US99/14447 on Jun. 25, 1999, which is a continuation-in-part of application No. 09/103,477, filed on Jun. 24, 1998, now abandoned.

(51) Int. Cl.$^7$ .................. C12N 15/87; C12N 15/00; C12N 15/09; C12Q 1/68; C07H 21/04
(52) U.S. Cl. ..................... 435/461; 435/6; 435/29; 435/320.1; 435/325; 435/455; 536/23.1
(58) Field of Search .................. 435/461, 455, 435/6, 29, 325, 320.1; 536/23.1

(56) References Cited

U.S. PATENT DOCUMENTS

| | | | |
|---|---|---|---|
| 5,019,034 A | | 5/1991 | Weaver et al. |
| 5,859,327 A | * | 1/1999 | Dev et al. ............. 800/205 |
| 5,944,710 A | * | 8/1999 | Dev et al. ............. 604/500 |
| 5,993,801 A | | 11/1999 | Greenberger et al. |

FOREIGN PATENT DOCUMENTS

| | | |
|---|---|---|
| WO | WO 97/07826 | 3/1997 |
| WO | WO 99/01158 | 1/1999 |

OTHER PUBLICATIONS

Luo, et al. Nature Biotechnology, Jan. 2000, vol. 18, pp. 33–37.*
Palu, et al. Journal of Biotechnology, 1999, vol. 68, pp. 1–13.*
Verma, et al. Nature, Sep. 1997, vol. 389, pp. 239–242.*
Yukiko Yamazaki et al, In Vivo Gene Transfer to Mouse Spermatogenic cells by Deoxyribonucleic Acid Injection into Seminiferous Tubules and Subsequent Electroporation, Biology Of Reproduction 59, 1439–1444 (1998).*
Andreason and Evans, Optimization of Electroporation . . . , Analytical Biochemistry 180, p269–274, Aug. 1, 1989.*

Andreason and Evans, "Optimization of Electroporation for Transfection of Mammalian Cell Lines," *Analytical Biochemistry* 180, 269–275 (1989).
Prausnitz et al., "Electroporation of mammalian skin: A mechanism to enhance transdermal drug delivery," Proc. Natl. Acad. Sci., Nov. 1993, vol. 90, pp. 10504–10508.
Giordano, Frank J. et al., "In vivo Gene Delivery to the Rabbit Carotid by Electroporation," *Supplement to Journal of the American College of Cardiology*, Abstract 1 page, Mar. 24–27, 1996.
Muramatsu, Tatsuo et al., "In Vivo Electroporation: A Convenient Method for Gene Transfer to Testicular Cells in Mice," *Anim. Sci. Technol. (Jpn)*, vol. 57, No. 11, pp. 975–982, 1996.
Nishi, Toru et al., "High–Efficiency in Vivo Gene Transfer Using Intraarterial Plasmid DNA Injection Following in Vivo Electroporation," *Cancer Res.*, vol. 56, pp. 1050–1055, 1996.
Nishi, Toru et al., "Treatment of Cancer Using Pulsed Electric Field in Combination with Chemotherapeutic Agents or Genes," *Human Cell*, vol. 10, No. 1, pp. 81–86, 1997.
Nishi, Toru et al., "High Efficiency Gene Transfer in Solid Tumors by In Vivo Electroporation," *Conference Supplement Cancer Gene Therapy*, vol. 4, No. 6, Abstract 1 page, Nov./Dec. 1997.
Nishi, T. et al., "High Efficiency Gene Transfer into Solid Tumors Using In Vivo Electroporation," *Proceedings of the American Association of Cancer Research*, vol. 39, Abstract p. 59, Mar. 1998.
Nomura, Masayuki et al., "In Vivo Induction of Cytotoxic T Lymphocytes Specific for a Single Epitope Introduced into an Unrelated Molecule," *Journal of Immunological Methods*, vol. 193, pp. 41–49, 1996.
Titomirov, Alexander V. et al., "In Vivo Electroporation and Stable Transformation of Skin Cells of Newborn Mice by Plasmid DNA," *Biochimica et Biophysica Acta.*, vol. 1088, pp. 131–134, 1991.
Aihara and Mlyazaki, "Gene transfer into muscle by electroporation in vivo," *Nature Biotechnology*, 16:867–870 (1998).

* cited by examiner

Primary Examiner—Gerry Leffers
(74) Attorney, Agent, or Firm—Douglas C. Murdock; Daniel M. Chambers; BioTechnology Law Group

(57) ABSTRACT

A method is provided for introducing nucleic acid into a cell, by contacting the cell with a nucleic acid and applying a low electrical field impulse for a long pulse length. A method is provided for introducing a polypeptide into a cell, by contacting the cell with the polypeptide and applying a low electrical field impulse for a long pulse length.

27 Claims, 2 Drawing Sheets

HIGH EFFICIENCY TRANSFECTION BASED ON LOW ELECTRIC FIELD STRENGTH, LONG PULSE LENGTH

This is a divisional of copending U.S. application Ser. No. 09/342,024, filed Jun. 28, 1999, which is the National Stage of International Application No. PCT/US99/14447, filed Jun. 25, 1999, which is a continuation-in-part of U.S. application Ser. No. 09/103,477, filed Jun. 24, 1998, now abandoned, each of which is incorporated by reference in the disclosure of this application.

FIELD OF THE INVENTION

The present invention relates generally to the use of electric pulses to increase the permeability of a cell and more specifically to the introduction of nucleic acids into a cell using electric pulses at a low electric field strength for a long pulse length.

BACKGROUND OF THE INVENTION

The ability to introduce foreign DNA into host cells on one of the principal tools of molecular biology. There are five general types of methods for transfecting eukaryotic host cells: (1) direct introduction of cloned DNA by microinjection, (2) use of viral vectors, (3) encapsulation in a carrier system such as a liposome, (4) the use of facilitators such as calcium phosphate or diethylaminoetyl (DEAE) dextran, and (5) electroporation. Although all of these methods allow the transfer of DNA into dividing cells, fewer methods are available for the transfer of DNA into non-dividing cells.

In the 1970's it was discovered that electric fields could be used to create pores in cells without causing permanent damage. This discovery made possible the insertion of large molecules into cell cytoplasm. It is known that genes and other molecules such as pharmacological compounds can be incorporated into live cells through a process known as electroporation. The genes or other molecules are mixed with the live cells in a buffer medium and short pulses of high electric fields are applied. The cell membranes are transiently made porous and the genes or molecules enter the cells, where they can modify the genome of the cell.

Studies have shown that large size nucleotide sequences (up to 630 kb) can be introduced into mammalian cells via electroporation (Eanault, et al., *Gene* (Amsterdam), 144(2):205, 1994; *Nucleic Acids Research*, 15(3): 1311, 1987; Knutson, et al., *Anal. Biochem.*, 164:44, 1987; Gibson, et al., *EMBO J.*, 6(8):2457, 1987; Dower, et al., *Genetic Engineering*, 12:275, 1990; Mozo, et al., *Plant Molecular Biology*, 16:917, 1991). However, the efficiency of electroporation, as reflected in the current literature, is low (see U.S. Pat. No. 5,019,034, herein incorporated by reference). A typical result is from 5 to 20 percent transfection depending on conditions, parameters and cell type. Creation of a high efficiency method for the transfer of nucleic acid via electroporation would make the method useful for the introduction of nucleic acid into cells both in vivo and in vitro.

SUMMARY OF THE INVENTION

The present invention provides a method for introducing nucleic acid into a cell by contacting the cell with a nucleic acid and applying a low voltage electrical impulse for a long pulse length. The electrical impulse is of sufficient duration and strength to introduce the nucleic acid into the cell. The method can be utilized in vitro or in vivo. The cells can be dividing or non-dividing.

The invention also provides a method for introducing polypeptides into a cell by contacting the cell with a polypeptide and applying a low electrical field impulse for a long pulse length. The electrical impulse is of sufficient duration and strength to introduce the polypeptide into the cell. The method can be utilized in vitro or in vivo. The cells can be dividing or non-dividing.

DESCRIPTION OF THE PREFERRED EMBODIMENTS

Figure 1:
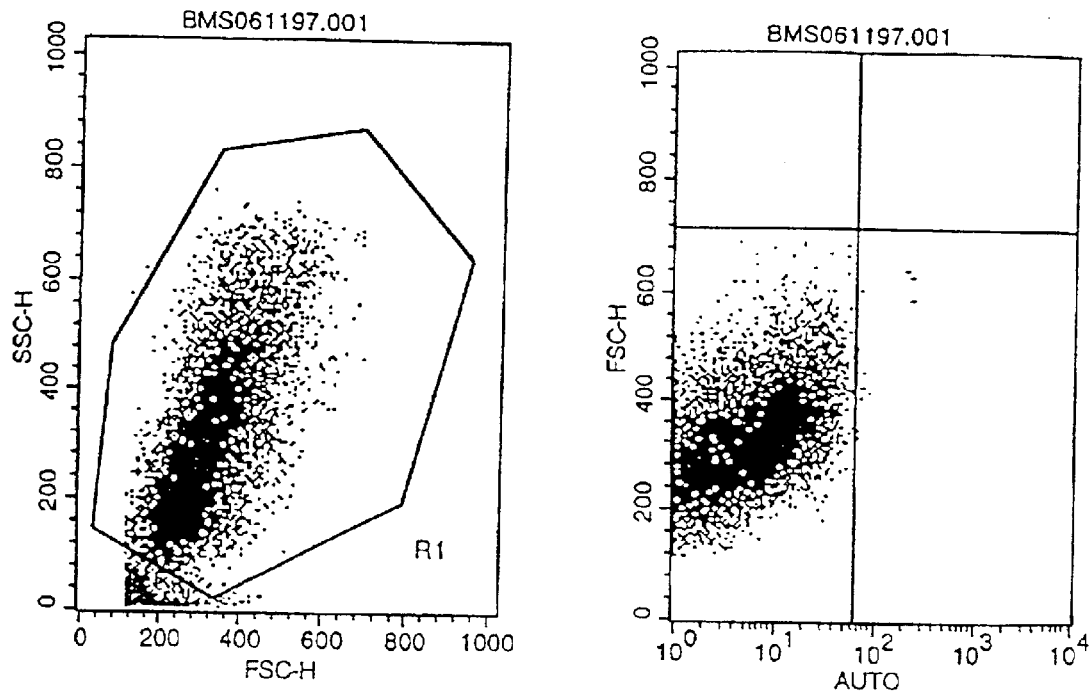
FIG. 1 shows the baseline conditions for the counting of GFP expressing cells representing the background for non-GFP expressing cells. To establish the level of "auto-fluorescence" background characteristics of a particular cell type, untreated cells are put through the FACS and a profile of their fluorescence is plotted as characterized by each cells forward scatter, (FSC-H) and side scatter (SSC-H). Each dot represent one event, or one cell, and the total number of cells counted is also calculated. From this data, the user can assign the areas of the quadrants. These quadrants are UL upper left, UR upper right, LL lower left, LR lower right. The % gated is the abundance of cells in that quadrant. In this example, the background fluorescence of the cells is completely contained within the LL quadrant.

It is to be understood that this invention is not limited to the particular methodology, protocols, sequences, models and reagents described as such may, of course, vary. It is also to be understood that the terminology used herein is for the purpose of describing particular embodiments only, and is not intended to limit the scope of the present invention which will be limited only by the appended claims.

All publications mentioned herein are incorporated herein by reference for the purpose of describing and disclosing the nucleic acids, cells, and methodologies which are described in the publications which might be used in connection with the presently described invention.

It is known that large size nucleotide sequences (up to 630 kb) can be introduced into mammalian cells via electroporation. However, the previous methodologies all utilize a high voltage electrical impulse to introduce nucleic acids into cells. The present invention is based on the finding that low electric field, long pulse length impulses introduces nucleic acid into cells at a very high efficiency. The invention provides a method for introducing nucleic acid into a cell by contacting the cell with a nucleic acid; and applying a low electrical field impulse for a long pulse length such that the nucleic acid is introduced into the cell.

The term "cell" includes any cell, including bacteria, yeast, fungi, plant, insect, and mammalian cells, amongst others. In a preferred embodiment, the cell is a mammalian cell. The method of the invention can be performed in cells present either in vivo or in vitro. The cells can be of any physiological system or tissue type. Non-limiting examples of mammalian cells that can be used with the subject invention in vivo and in vitro are the cells of the immune system, neuroendocrine system, circulatory system, skeletomuscular system, reproductive system, amongst others. All cell types can be used with the method of the invention, including, but not limited to, hematopoietic cells, tumor cells, skin cells, vascular cells, lymphocytes, endocrine cells, neuronal cells, glial cells, fibroblasts and stromal cells, amongst many others. An advantage of the method of the invention is that both dividing or nondividing can be transfected by a method of the invention. In vitro, cells of use in the method of the present invention include cells of any cell type, and includes both primary cultures of cells and cell lines. In vitro, cells to be transfected may be in suspension in a static condition (e.g., a static chamber, such as a cuvette) attached as a monolayer to a culture dish, or in a continuous, i.e., "flow-through" electroporation chamber (e.g., U.S. Pat. Nos. 5,545,130 and 5,676,646).

By "transformation" is meant a genetic change induced in a cell following incorporation of new nucleic acid (i.e., nucleic acid exogenous to the cell), polymer or oligonucleotide. Where the cell is a mammalian cell, the genetic change may be achieved by introduction of the nucleic acid into the genome of the cell (i.e., stable transformation) or by the introduction of the nucleic acid such that it is not incorporated into the genome of the cell (transient transformation). The term "transfection" as used herein refers to the process of introducing nucleic acids into a host cell, without the use of a virus or viral particle carrier. By "transformed cell" is meant a cell into which, or into an ancestor of which, has been introduced a previously exogenous nucleic acid sequence.

In a method of the invention, a cell is contacted with a nucleic acid. "Contacting" can occur in the presence of a media for cell growth in vitro. A media for cell growth can be a standard medium, which is used for the culture of a broad spectrum of cell lines and tissues (e.g., Dulbecco's Modified Eagles Medium), or a basal medium, which consists of the essential elements of amino acids, sugars, vitamins, ions, and trace elements (e.g., Basal Modified Eagles Medium), or a specialty medium, which has been developed for the culture of a narrow spectrum of cells. The medium can be supplemented with growth factors, amino acids, antibiotics, hormones, and other supplements known in the art. For the transformation of mammalian cells, serum can also be used to supplement the media as 2–20% by volume. The serum can be isolated from any mammalian species, and includes but is not limited to calf, human, goat, sheep, pig, and rat serum. The serum may be fetal serum. Preferably, the serum is fetal calf serum. Most preferably, 2% fetal calf serum is added to the medium during the process of transfection.

In vivo, "contacting" occurs by administering the nucleic acid via injection or perfusion. Preferably, the subject is a mammalian subject, more preferably, the subject is a human subject. In a mammalian subject, the nucleic acid can be administered intravenously, intra-arterially, intraperitoneally, intramuscularly, subcutaneously, intracavity, intralesionally, or transdermally. Preferably the nucleic acid is administered at or near the site of electroporation. In a preferred embodiment, the nucleic acid is administered intravascularly. Preparations for administration include sterile aqueous or non-aqueous solutions, suspensions and emulsions. Examples of aqueous carriers include water, alcoholic/aqueous solutions, emulsions or suspensions, including saline and buffered media. Vehicles include sodium chloride solution, Ringer's dextrose, dextrose and sodium chloride, lactated Ringer's or fixed oils. Non aqueous solvents are propylene glycol, polyethylene glycol, vegetable oils such as olive oil, and injectable organic esters such as ethyl oleate. Intravenous vehicles include fluid and nutrient replenishers, electrolyte replenishers (such as those based on Ringer's dextrose), and the like. Preservative and other additives may also be present, for example, antimicrobials, anti-oxidants, chelating agents, and inert gases and the like.

The term "nucleic acid" or "nucleic acid sequence" or "polynucleotide" refers to a polymeric form of nucleotides at least 10 bases in length, and can range to greater than one hundred kilobases (kb) in length. The nucleic acid sequence can encode a polypeptide. By "isolated nucleic acid sequence" is meant a nucleic acid sequence that is not immediately contiguous in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleic acids of the invention can be ribonucleotides, deoxyribonucleotides, or modified forms of either nucleotide. The term includes both single and double stranded forms of polymers. When double-stranded DNA is used in the method of the subject invention it can be of any form, including but not limited to linear, circular, and supercoiled forms. Preferably, when double stranded DNA is used it is of the supercoiled form.

It may further be desirable to modulate the expression of a gene in a cell by the introduction of a nucleic acid sequence by the method of the invention. The term "modulate" envisions the suppression of expression of a gene when it is overexpressed, or augmentation of expression when it is underexpressed. For example, where a cell proliferative disorder is associated with the expression of a gene, nucleic acid sequences that interfere with the gene's expression at the translational level can be used. This approach utilizes, for example, antisense nucleic acid, ribozymes, or triplex agents to block transcription or translation of a specific mRNA, either by masking that mRNA with an antisense nucleic acid or triplex agent, or by cleaving it with a ribozyme.

Antisense nucleic acids are DNA or RNA molecules that are complementary to at least a portion of a specific mRNA molecule (Weintraub, *Scientific American*, 262:40, 1990). In the cell, the antisense nucleic acids hybridize to the corresponding mRNA, forming a double-stranded molecule. The antisense nucleic acids interfere with the translation of the mRNA, since the cell will not translate a mRNA that is double-stranded and also induce nuclease cutting of the hybrid molecule. Antisense oligomers of about 15-20 nucleotides are preferred, since they are easily synthesized and are less likely to cause problems than larger molecules when introduced into the target cell, but are long enough to provide specificity for their target. The use of antisense methods to inhibit the in vitro translation of genes is well known in the art (Marcus-Sakura, *Anal. Biochem.*, 172:289, 1988).

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., *Antisense Res. and Dev.*, 1(3):227, 1991; Helene, C., *Anticancer Drug Design*, 6(6):569, 1991).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J Amer. Med. Assn.*, 260:3030, 1988). A major advantage of this approach is that, because they are sequence-specific, only mRNAs with particular sequences are inactivated.

There are two basic types of ribozymes namely, tetrahymena-type (Hasselhoff, *Nature*, 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

The nucleic acids of use with the subject invention can encode any peptide or polypeptide. For example, therapeutic peptides or polypeptides, immunomodulatory agents, and other biological response modifiers can be administered for incorporation by a cell using the method of the invention. A "therapeutic" peptide or polypeptide is any peptide or polypeptide which can be used to prevent, to cure or at least partially arrest a deficiency in a cell. The term "biological response modifiers" is meant to encompass substances which are involved in modifying the immune response. Examples of immune response modifiers include such compounds as lymphokines. Lymphokines include, but are not limited to, tumor necrosis factor, interleukins 1, 2, and 3, and 12, lymphotoxin, macrophage activating factor (MAF), migration inhibition factor (MIF), colony stimulating factor (CSF), and alpha-interferon, beta-interferon, and gamma-interferon and their subtypes. Also included are nucleic acid sequences which encode metabolic enzymes and proteins, including antihaemophilic compounds, e.g., Factor VIII or Factor IX. Other exemplary, non-limiting nucleic acids of interest include DNA encoding insulin, growth factors (e.g., growth hormone, insulin-like growth factor-I (IGF-I), platelet-derived growth factor (PDGF), epidermal growth factor (EGF), acidic fibroblast growth factor, basic fibroblast growth factor, or transforming growth factor β), cytokines (e.g., interferon (INF) (e.g., INF-α2b, INF-α2a, INF-αN1, INF-α1b, INF-γ, interleukin (e.g., IL-2, IL-8), or tumor necrosis factor (TNF) (e.g., TNF-α, TNF-β)), clotting factors (e.g. clotting factor VIII), hormones (e.g., GP-1), antimicrobial polypeptides (e.g., antibacterial, antifungal, antiviral, and/or antiparasitic polypeptides), enzymes (e.g., adenosine deaminase), filgastim (Neupogen), hemoglobin, erythropoietin, insulinotropin, imiglucerase, sarbramostim, antigens, tissue plasminogen activator (tPA), urokinase, streptokinase, endothelian, soluble CD4, and antibodies and/or antigen-binding fragments (e.g., FAbs) thereof (e.g., orthoclone OKT-e (anti-CD3), GPIIb/IIa monoclonal antibody).

The nucleic acids of use with the subject invention can be any DNA encoding any protein for which introduction into a cell or subject is desirable. A subject is any mammal, preferably human. For example, the methods of the invention can be used to introduce nucleic acid into mammalian cells having an inherited or acquired disease associated with a specific protein deficiency (e.g., diabetes, hemophilia, anemia, severe combined immunodeficiency). Such protein deficient states are amenable to treatment by the introduction of nucleic acid, i.e., expression of a protein to restore the levels of the protein to at least normal. The nucleic acids of use with the methods of the invention may encode a polypeptide that is either normally present in a normal cell or which is foreign to the cell, and which polypeptide is effective in treatment of a condition by expression or over-expression of the polypeptide. For example, the DNA of interest can encode antimicrobial, antiparasitic, antifungal, or antiviral polypeptides for treatment of a mammalian cell having a viral (e.g., human immunodeficiency virus (HIV), Epstein-Barr virus (EBV), herpes simplex virus (HSV), bacterial, fungal, and/or parasitic infection, either where the infection is chronic, i.e., persisting over a relatively long period of time, or acute.

The nucleic acids of use with the method of the invention may also be used to enhance or supplement expression of a protein normally present in a cell, or to express a protein not normally present in a normal cell, in order to achieve a desired effect (e.g., to enhance a normal metabolic process). The DNA sequence of interest may originate from the same species as the cell being treated or may originate from a different species.

Table 1 provides a list of exemplary proteins and protein classes which can be delivered by the method of the invention. This list is only exemplary and is not meant to be limiting.

TABLE 1

Exemplary Proteins and Protein Classes
SPECIFIC EXEMPLARY PROTEINS

| | |
|---|---|
| insulin | interferon-α2B |
| human growth hormone (hGH) | transforming growth factor (TGF) |
| erythropoietin (EPO) | ciliary neurite transforming factor (CNTF) |
| clotting factor IX | insulin-like growth factor-1 (IGF-1) |
| bovine growth hormone (BGH) | granulocyte macrophage colony stimulating factor (GM-CSF) |
| platelet derived growth factor (PDGF) | interferon-α2A |
| clotting factor VIII | brain-derived neurite factor (BDNF) |
| thrombopoietin (TPO) | insulintropin |
| IL-1 | tissue plasminogen activator (tPA) |
| IL-2 | urokinase |
| IL-1 RA | streptokinase |
| superoxide dismutase (SOD) | adenosine deamidase |
| catalase | IL-12 |
| fibroblast growth factor (FGF) (acidic or basic) | arginase |
| neurite growth factor (NGF) | phenylalanine ammonia lyase |
| granulocyte colony stimulating factor (G-CSF) | γ-interferon |
| L-asparaginase | pepsin |
| uricase | trypsin |
| chymotrypsin | elastase |
| carboxypeptidase | lactase |
| sucrase | intrinsic factor |
| calcitonin | parathyroid hormone(PTH)-like hormone |
| Ob gene product | cholecystokinin (CCK) |
| glucagon | insulinotrophic hormone |
| proteases | pituitary hormones |
| protease inhibitors | growth factors |
| cytokines | somatomedians |
| chemokines | immunoglobulins |
| gonadotrophins | interleukins |
| chemotactins | interferons |
| lipid-binding proteins | channel proteins |

Numerous nucleic acids have been isolated and are well known in the art which can be used with the methods of the invention. For example, the sequence of the DNAs encoding insulin, human growth hormone, intrinsic factor, clotting factor VIII, and erythropoietin are available from Genbank and/or have been described in the scientific literature (e.g., human clotting factor VIII gene: Gitschier et al., *Nature* 312:326–330, 1984; Wood et al., *Nature* 312:330–337, 1984; human intrinsic factor: Hewitt et al., *Genomics* 10:432–440, 1991). Other nucleic acids encoding polypeptides that are of use with the method of the invention are disclosed in, for example, the Physicians' Desk Reference (1994 Physicians' Desk Reference, 48th Ed., Medical Economics Data Production Co., Montvale, N.J.; incorporated by reference).

Any nucleic acid can be delivered by the method of the invention. Where the nucleic acid encoding a protein of interest has not been isolated, this can be accomplished by various, standard protocols well known to those of skill in the art (see, for example, Sambrook et al., supra; Suggs et al., *Proc. Natl. Acad. Sci. USA* 78:6613–6617, 1981; U.S. Pat. No. 4,394,443; each of which are incorporated herein by reference with respect to identification and isolation of nucleic acid encoding a protein of interest). For example, genomic or cDNA clones encoding a specific protein can be isolated from genomic or cDNA libraries using hybridization probes designed on the basis of the nucleotide or amino acid sequences for the desired gene. The probes can be constructed by chemical synthesis or by polymerase chain reaction (PCR) using primers based upon sequence data to amplify DNA fragments from pools or libraries (see U.S. Pat. Nos. 4,683,195 and 4,683,202). Nucleotide substitutions, deletions, additions, and the like can also be incorporated into the polynucleotides, so long as the ability of the polynucleotide to hybridize is not substantially disrupted. (Sambrook et al. supra). The clones may be expressed or the DNA of interest can be excised or synthesized for use in other constructs. If desired, the DNA of interest can be sequenced using methods well known in the art.

It may also be desirable to utilize nucleic acid encoding altered forms of proteins. For example, nucleic acids encoding polypeptides which are protease resistant or have enhanced activity relative to the wild-type protein may be utilized with the method of the invention. Alternatively, nucleic acid encoding a protein with altered ability to form dimers or multimeric complexes may be used with the method of the invention. For example, a nucleic acid encoding a modified insulin which has altered dimerization could be utilized.

The nucleic acid used in the method of the invention may encode an antibody molecule. The preparation of monoclonal antibodies and nucleic acid encoding monoclonal antibodies is conventional. See, for example, Kohler & Milstein, 1975, *Nature* 256:495; Coligan et al., sections 2.5.1–2.6.7; and Harlow et al, in: *Antibodies: a Laboratory Manual*, page 726 (Cold Spring Harbor Pub. 1988), which are hereby incorporated by reference. The nucleic acid used in the method of the invention may also encode a humanized antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., 1989, *Proc. Nat'l Acad. Sci. USA* 86:3833, which is hereby incorporated in its entirety by reference. Techniques for producing humanized monoclonal antibodies are described, for example, by Jones et al., 1986, *Nature* 321:522; Riechmann et al., 1988, *Nature* 332:323; Verhoeyen et al, 1988, *Science* 239:1534; Carter et al., 1992, *Proc. Nat'l Acad. Sci. USA* 89:4285; Sandhu, 1992, *Crit. Rev. Biotech.* 12:437; and Singer et al., 1993, *J. Immunol.* 150:2844, which are hereby incorporated by reference.

Nucleic acids encoding antibodies of use with the method of the invention also may encode human antibody fragments isolated from a combinatorial immunoglobulin library. See, for example, Barbas et al., 1991, in: *Methods: a Companion to Methods in Enzymology*, Vol. 2, page 119; Winter et al., 1994, *Ann. Rev. Immunol.* 12:433, which are hereby incorporated by reference. Cloning and expression vectors that are useful for producing a human immunoglobulin phage library can be obtained, for example, from STRATAGENE Cloning Systems (La Jolla, Calif.).

The term "antibody" includes intact molecules as well as fragments thereof, such as Fab, F(ab')$_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, *Antibodies: A Laboratory Manual*, Cold Spring Harbor Laboratory, New York (1988), incorporated herein by reference). As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Nucleic acid sequences of use with the method of the invention also include those which encode a selectable marker. As used herein, the term "marker" refers to a gene encoding a trait or a phenotype which permits the selection of, or the screening for, a cell containing the marker. Preferably, the marker gene is an antibiotic resistance gene whereby the appropriate antibiotic can be used to select for transformed cells from among cells that are not transformed.

Examples of suitable selectable markers include adenosine deaminase, dihydrofolate reductase, hygromycin-B-phosphotransferase, thymidine kinase, xanthine-guanine phosphoribosyl-transferase and amino-glycoside 3'-O-phosphotransferase II (kanamycin, neomycin and G418 resistance). Also included are genes which encode markers detectable by other means such as their emission spectra. For example, green fluorescent protein (GFP) can be detected by its fluorescence spectra. Other suitable markers are well known to those of skill in the art.

Nucleic acid sequences which encode a polypeptide can be operatively linked to expression control sequences. "Operatively linked" refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, as start codon (i.e., ATG) in front of a protein-encoding gene, splicing signal for introns, maintenance of the correct reading frame of that gene to permit proper translation of mRNA, and stop codons. The term "control sequences" is intended to included, at a minimum, components whose presence can influence expression, and can also include additional components whose presence is advantageous, for example, leader sequences and fusion partner sequences. Expression control sequences can include a promoter.

By "promoter" is meant minimal sequence sufficient to direct transcription. Included are those promoter elements which are sufficient to render promoter-dependent gene expression controllable for cell-type specific or tissue-specific expression. Also included are promoter elements which are inducible by external signals or agents. These elements may be located in the 5' or 3' regions of the gene. Both constitutive and inducible promoters, are included (see, e.g., Bitter et al., *Methods in Enzymology* 153:516–544, 1987). For example, in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the nucleic acid sequences of the invention.

In the present invention, the nucleic acid sequence encoding a polypeptide may be inserted into an expression vector which contains a promoter sequence which facilitates the efficient transcription of the inserted genetic sequence in the cell following the introduction of the nucleic acid into the cell. The expression vector typically contains an origin of replication, a promoter, as well as specific genes which allow phenotypic selection of the transformed cells. Delivery of nucleic acid sequences can be achieved using "naked" DNA. "Naked" DNA is deoxyribonucleic acid that is not contained in a virus particle nor is it associated with lipids or other chemical formulations. The use of "naked" DNA eliminates the antigenic problems of viral vectors and the toxicity of lipids.

For use in the subject invention, the nucleic acid can be purified. Many purification methods for nucleic acid are known to one of skill in the art (see Sambrook, T., et al., *Molecular Cloning: A Laboratory Manual*, Cold Spring Harbor laboratory Press, New York, 1989). For example, nucleic acid used with the method of the invention can be purified by density separation on a cesium chloride gradient. Preferably, the DNA is purified such that it is endotoxin-free. By "endotoxin" is meant a heat-stable toxin associated with the outer membranes of certain Gram-negative bacteria, including the enterobacteria, brucellae, neisseriae, and vibrios. Endotoxin, normally released upon disruption of the bacterial cells, is composed of lipopolysaccharide molecules (LPS) and any associated proteins. The phospholipid moiety of LPS, lipid a, is associated with LPS toxicity. When injected in large quantities endotoxin produces hemorrhagic shock and severe diarrhea; smaller amounts cause fever, altered resistance to bacterial infection, leukopenia followed by leukocytosis, and numerous other biologic effects. The terms "endotoxin," "LPS," and "lipopoly-saccharide" as used herein are essentially synonymous. By "endotoxin-free" is meant that the nucleic acid is substantially separated from any endotoxin. Typically the nucleic acid is "endotoxin-free" when at least 60% of the endotoxin found in a crude preparation is removed. Preferably, at least 75% of the endotoxin is removed, more preferably at least 90%, and most preferably at least 99% of the endotoxin is removed from the nucleic acid. Methods are well known in the art to purify DNA from endotoxin, and several kits are commercially available to produce endotoxin-free DNA. For example, Qiagen columns and Qiagen endotoxin-free plasmid preparation kits may be used.

The invention further provides a method of introducing a polypeptide into a cell by contacting the cell with a polypeptide; and applying a low electrical field impulse for a long pulse length, such that the impulse is of sufficient duration and strength to introduce the polypeptide into the cell. A "polypeptide" consists of five or more covalently linked amino acids. For use with the subject invention a crude cellular fraction can be used, or the polypeptide can be substantially purified. The term "substantially purified" as used herein refers to a polypeptide which is substantially free of other proteins, lipids, carbohydrates or other materials with which it is naturally associated. One skilled in the art can purify polypeptides using standard techniques for protein purification (e.g., Lehninger, "Biochemistry," Second Edition, Worth Publishing, New York, 1975, p. 157–182, herein incorporated by reference). A substantially pure polypeptide will yield a single major band on a non-reducing polyacrylamide gel. The purity of a polypeptide can also be determined by amino-terminal amino acid sequence analysis.

The method of the subject invention can be used to introduce intact functional polypeptides or functional fragments of a polypeptide. As used herein, the term "functional polypeptide" refers to a polypeptide which possesses biological function or activity which is identified through a defined functional assay and which is associated with a particular biologic, morphologic, or phenotypic alteration in the cell. The term "functional fragments of a polypeptide," refers to all fragments of a polypeptide that retain an activity of the peptide, e.g., the ability to activate transcription, the ability to bind a receptor, or the ability to be recognized by a monoclonal antibody. Biologically functional fragments, for example, can vary in size from a polypeptide fragment as small as an epitope capable of binding an antibody molecule to a large polypeptide capable of participating in the characteristic induction or programming of phenotypic changes within a cell.

When a cell is placed in an electrical field, an electrical potential is induced across the cell membrane. For a spherical cell, the membrane potential induced by an electrical field is:

$$V_m = 1.5rE \cos \theta$$

where R is the radius of the cell, E is the strength of the external field and $\theta$ is the angle between the direction of the external field and the normal vector of the membrane at a the specific site (see U.S. Pat. No. 4,822,470, herein incorporated by reference).

The induced electric field within the membrane is:

$$E_m = V_m/d = 1.5(r/d)E \cos \theta$$

where d is the thickness of the membrane, and by definition is smaller than r. The electric field in the membrane exerts a strong force on the membrane, such that pores will be formed. The pores induced by the electric field are reversible, an introduction of molecules such as nucleic acid is possible, and most of the cells can remain viable.

In the method of the invention, a low electrical field impulse is applied for a long pulse length to the cells in the method of the invention, such that the nucleic acid or polypeptide is introduced into the cell. The electrical impulse can be generated by any pulse generator. Pulse generators for carrying out the method of the invention are and have been available on the market for a number of years. One suitable signal generator is the ELECTRO SQUARE PORATOR MODEL T820 commercially available from BTX, a division of Genetronics, Inc., of San Diego, Calif. U.S.A. The T820 signal generator generates a pulse from the in-complete discharge of a capacitor which results in a square waveform. The electric signal generated by this signal generator is characterized by a fast rise time and constant voltage over the duration of the pulse length.

The application of an electrical field across the membrane of a cell results in the creation of transient pores which are critical to the electroporation process. The T820 signal generator provides the voltage (in kV) that travels across the gap (in cm) between the electrodes. This potential difference defines what is called the electric field strength where E equals kV/cm. Each cell has its own critical field strength for optimum electroporation. This is due to cell size, membrane makeup and individual characteristics of the cell wall itself. For example, mammalian cells typically require between 0.5 and 5.0 kV/cm before cell death and/or electroporation occurs. Generally, the required field strength varies inversely with the size of the cell.

The waveforms of the voltage pulse provided by the generator in the power pack can be an exponentially decaying pulse, a square pulse, a unipolar oscillating pulse train or a bipolar oscillating pulse train, for example. Preferably, the waveform used for the method of the invention is a square pulse. The voltage applied between the at least first and second electrode is sufficient to cause electroporation of the cell. The field strength is calculated by dividing the voltage by the distance (calculated for 1 cm separation; expressed in cm) between the electrodes. For example, if the voltage is 500 V between two electrode faces which is ½ cm apart, then the field strength is 500/(½) or 1000 V/cm or 1 kV/cm. In the method of the invention, the amount of voltage applied between the electrodes is of a low voltage. Preferably, the amount of voltage applied between the electrodes is in the range of about 300 volts per centimeter to 600 volts per centimeter, and preferably from about 400 volts per centimeter to 500 volts per centimeter. The low electrical field impulse is applied for a long pulse length in the method of the invention. The pulse length can be 10 milliseconds (ms) to 100 ms, and preferably is from about 50 ms to 100 ms. Without being bound by theory, the long pulse length allows the nucleic acid to be "loaded" into the opened pores via an electrophoretic event, and the number of plasmids delivered to each cell is much higher than achieved by other pulse parameters. Thus a higher percentage of cells are transfected and a high level of gene expression can be achieved.

Many conventional electroporation protocols have used relatively high electric fields (>2,000 V/cm) delivered in a very short pulse (<1 ms). This can be delivered in the form of an exponentially decaying pulse or as a uniform "square" wave. It is well recognized in the art that when using such parameters there is a relationship between increased voltage and the efficiency of gene delivery. However, at these voltages benefits of increased efficiency are offset by increased cell death, which is limiting for applications where larger numbers of viable cells are desired.

There can be from about 1 to 10 pulses applied to an area or group of cells. The waveform, electric field strength and pulse duration are dependent upon the exact construction of the delivery device and types of cells used in the electroporation procedure. One of skill in the art would readily be able to determine the appropriate number of pulses useful in the method of the invention by measuring transformation efficiency and cell survival using methods well known in the art.

The electrical impulse can be applied while the cells are at any temperature, generally the electrical pulse will be applied while the cells are at a temperature from about 2° C. to 390° C. Preferably, the electrical impulse is applied while the cells are at about 2° C. to 10° C. Following the electrical impulse, the cells can be incubated for a period of time prior to plating or analyzing the cells. Preferably, the cells are incubated at a temperature of about 37° C.

The following examples are intended to illustrate but not limit the invention. While they are typical of those that might be used, other procedures known to those skilled in the art may alternatively be used.

EXAMPLE 1

TRANSFECTION PROTOCOL

Establishment of Human Long Term Bone Marrow Cultures (LTMBC)

Cultures were initiated from aspirates of human bone marrow obtained using standard procedures (Kuznetsov, S. A., et al., *Brit. J. Haem.* 79:561–570, 1997). After lysis of red cells and subsequent washing steps, unfractionated nucleated bone marrow cells were cultured in McCoy's 5A medium (Life Technologies, ON, Canada) containing 16.5% fetal calf serum (FCS), 1% glutamine, 1% sodium pyruvate, 1% sodium carbonate, 1% vitamins, 0.8% essential and 0.4% nonessential amino acids (Life Technologies, ON, Canada). Cultures were maintained at 37° C. in a 5% humidified $CO_2$ environment. Cells were passaged when approaching confluence and replated in medium containing 20 U/ml interleukin-1 and 0.5 ng/ml bFGF (R&D Systems, Minneapolis, Minn.). Cultures were subsequently reexpanded and passaged several times (typically about 4–5). During this time residual hematopoietic cells within the culture are lost, leaving a relatively pure, adherent stromal culture. This also allowed for considerable expansion of numbers of stromal cells (greater than $10^8$ stromal cells from a 5–10 ml bone marrow aspirate. When dividing cells were used in the experiments, the cells were passaged 2–4 days prior to electroporation to ensure that the cells in the culture were dividing (nonconfluent).

Constructs for Electroporation

Constructs were prepared using nucleic acid sequences encoding the green fluorescent protein (GFP) as a marker for cell transfection. This protein is autofluorescent and requires no substrate for activity. A construct, pEGFP-C1, was prepared in which GFP was placed under the control of the cytomegalovirus (CMV) promoter, which is a strong retroviral promoter that is highly expressed in most cells.

Electroporation

A T820(BTX) electroporation instrument was used to perform the procedure. The electroporation was performed in a cuvette with parallel electrodes separated by a 4 mm gap. The T820 generates a square wave that has been found to be superior than a exponential wave shape in delivering nucleic acid sequences to cells. The square wave has the advantage of maintaining the set voltage for a sustained period, which, without being bound by theory, produces the electrophoretic effect of moving DNA through the opened pores. The voltage settings were set between 150–200 volts (400–500 V/cm), with a pulse length of 50–70 ms. One pulse was delivered to the cells.

Nucleic Acid Purification

The nucleic acid sequences were purified using several methods. The highest efficiency transformation was obtained using supercoiled plasmid DNA prepared in JM-109 host *E. coli* bacteria. The DNA was purified using either a Qiagen column or a Qiagen endotoxin-free plasmid preparation kit.

The quality of the nucleic acid used in the electroporation protocol had a large impact on the efficiency of transfection and on cell survival. In general, less pure preparations resulted in a lower gene transfer efficiency and seemed to contribute to increased cell death. It should be noted that routine assays of DNA quality such as optical density ratios (e.g., $OD_{260}/OD_{280}$) did not predict transfection efficiency.

Optimally, 40–50 µg of plasmid was used per 4 million cells.

Media

Electroporation was performed in whole cell media supplemented with 2% fetal calf serum. In general, the media selected was the media normally used to culture the cell. Transfection efficiency was lower in whole media that was not supplemented with fetal calf serum; the addition of fetal calf serum caused higher transfection efficiencies. Addition of serum increased the ratio of transfected cells to untransfected cells and also increased overall cell survival.

Effects of Temperature

Cells were mixed with the DNA, placed in a cuvette, and placed on ice for ten minutes. The cuvette was then put into the electroporation chamber and pulsed. The cuvette was then removed from the electroporation chamber and placed in a water bath preheated to 37° C. The cuvette was maintained at 37° C. for ten minutes and the cells were then plated in whole media, which was supplemented with 10–20% fetal calf serum and other added growth factors and supplements. The rapid warming of cells to 37° C. increased the cell survival and increased transfection efficiency. Without being bound by theory, the rapid warming of the cells closes the open pores in the cells, and thus increases the survival and transfection efficiency.

Results

Figure 2:
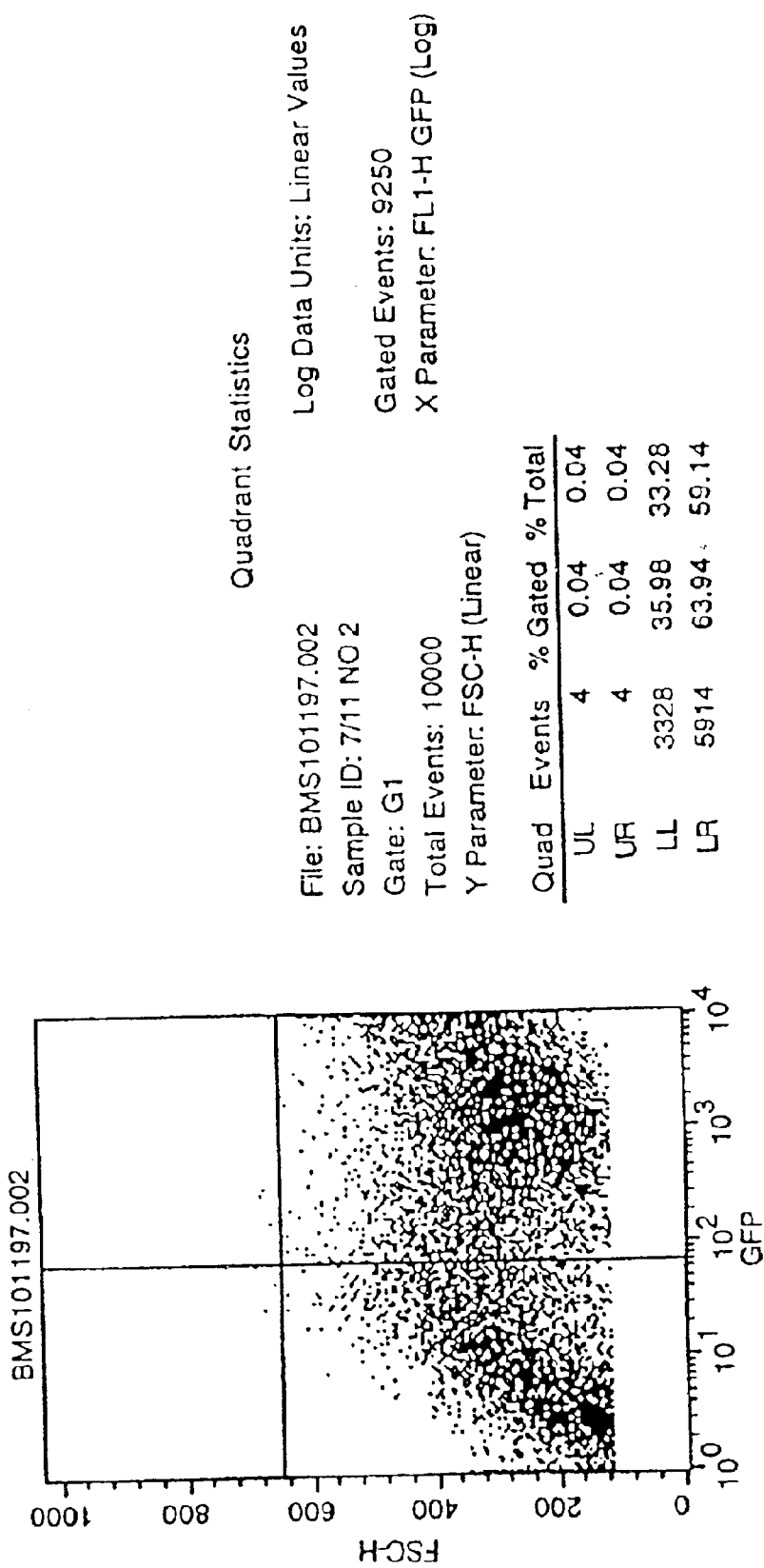
FIG. 2 shows an analysis of GFP expression in human stromal cells transfected using the latest optimized protocol. Supercoiled GFP plasmids were used in a transfection experiment done as discussed in the examples. These results, when analyzed by FACS, show a transfected stromal cell population that is ~64% positive for GFP. This current protocol uses 100 volts across an 0.2 cm cuvette with a 70 ms pulse duration.

Measurements of baseline (background) fluorescence demonstrated that greater than 99% of the background was found in the lower left (LL) quadrant. (FIG. 1). Following electroporation, using the conditions described above, greater than 60% GFP positive transfection was achieved. (FIG. 2). Cell survival levels were >60%. In addition, it was noted that the level of GFP expression on a per cell basis was much higher than that obtained using a standard transfection method, such as calcium phosphate precipitation.

A variety of parameters were shown to be critical for transfection efficiency. For example, the level of endotoxin contained in the DNA preparation effected transfection efficiency. Linearizing the DNA also had a negative effect on transfection efficiency. The parameters are synergistic. In a specific non-limiting example, elimination of one parameter (such as the use of endotoxin-free DNA) resulted in a large reduction in transfection efficiency.

The levels of transfection achieved were comparable to the transfection efficiencies obtained with viral vectors. However, the electroporation technique worked on a broader range of cell types than the viral vectors. Specifically, electroporation could be used to transfect nondividing cells. Electroporation can also be used to transfect cell types that are refractory to viral mediated transfection.

From the above description, the essential characteristics of the present invention can be ascertained. Without departing from the spirit and scope thereof, various changes and modifications of the invention can be made to adapt it to various usages and conditions. Thus, other embodiments are also within the claims.

What is claimed is:

1. A method for introducing a nucleic acid into a cell of a mammalian subject in vitro, comprising: contacting the cell outside of a subject's body with an isolated nucleic acid sequence and applying to the cell a low electrical field impulse of about 300 volts per centimeter to about 600 volts per centimeter for a long pulse length of about 10 milliseconds to about 100 milliseconds, wherein the impulse is of sufficient duration and strength to allow introduction of the nucleic acid into the cell.

2. The method of claim 1, wherein the contacting occurs in the presence of a media for cell growth supplemented with calf serum.

3. The method of claim 2, wherein the calf serum is fetal calf serum.

4. The method of claim 2, wherein the media is supplemented with 2% fetal calf serum.

5. The method of claim 2, further comprising incubating the cell in a media containing a member of the group selected from fetal calf serum, growth factors, and antibiotics.

6. The method of claim 1, wherein said applying occurs at a temperature of about 2° C. to about 10° C.

7. The method of claim 1, wherein the low electrical field impulse is from about 400 volts to about 500 volts per centimeter.

8. The method of claim 1, wherein the electrical impulse is applied over about 50 milliseconds to about 75 milliseconds.

9. The method of claim 1, wherein the electrical impulse is selected from the group consisting of a square wave pulse, an exponential wave pulse, a unipolar oscillating wave form, and a bipolar oscillating wave form.

10. The method of claim 1, wherein said electrical impulse is comprised of a square wave pulse.

11. The method of claim 1, wherein the electrical impulse applied is from about 1 to about 10 electrical pulses.

12. The method of claim 1, wherein the nucleic acid is supercoiled.

13. The method of claim 1, wherein the nucleic acid is endotoxin-free.

14. The method of claim 1, further comprising incubating the cell after the electroporation procedure at about 37° C.

15. The method of claim 1, wherein the cell is a nondividing cell.

16. The method of claim 1, wherein the cell is a dividing cell.

17. The method of claim 1, wherein the cell is a hematopoietic cell.

18. The method of claim 1, wherein the cell is a stromal cell.

19. A method of claim 1, wherein the cell is a muscle cell.

20. A method of claim 1, wherein the cell is a vascular cell.

21. A method of claim 1, wherein the cell is a skin cell.

22. A method of claim 1, wherein the cell is a tumor cell.

23. A method of claim 1, wherein the nucleic acid modulates the expression of a gene in the cell.

24. A method of claim 1, wherein the nucleic acid encodes an immunomodulatory agent.

25. A method of claim 1, wherein the nucleic acid encodes a protein.

26. A method of claim 25, wherein the nucleic acid encodes a protein selected from the group consisting of a biological response modifier, a therapeutic protein, an enzyme, an antibody, and an antigen binding fragment of an antibody.

27. A method of claim 1, wherein the nucleic acid encodes an antibody molecule.

* * * * *